United States Patent [19]

Akimoto et al.

[11] Patent Number: 5,496,946

[45] Date of Patent: Mar. 5, 1996

[54] PRODUCTION OF PYRROLOPYRIMIDINES AND INTERMEDIATES THEREFOR

[75] Inventors: Hiroshi Akimoto, Kobe; Takenori Hitaka, Takarazuka; Tetsuo Miwa, Kobe, all of Japan

[73] Assignee: Takeda Chemical Industries, Ltd., Osaka, Japan

[21] Appl. No.: 257,512

[22] Filed: Jun. 9, 1994

Related U.S. Application Data

[62] Division of Ser. No. 29,310, Mar. 8, 1993, Pat. No. 5,349,064, which is a continuation of Ser. No. 537,807, Jun. 14, 1990, abandoned.

[30] Foreign Application Priority Data

Jun. 14, 1989 [JP] Japan .................................... 1-150910
Sep. 18, 1989 [JP] Japan .................................... 1-242975
Apr. 6, 1990 [JP] Japan .................................... 2-092391

[51] Int. Cl.$^6$ ........................ C07D 239/50; C07D 239/48
[52] U.S. Cl. ........................................... 544/321; 544/325
[58] Field of Search ..................................... 544/321, 325

[56] References Cited

FOREIGN PATENT DOCUMENTS

| | | |
|---|---|---|
| 0268377 | 5/1988 | European Pat. Off. . |
| 0325343 | 7/1989 | European Pat. Off. . |
| 0334636 | 9/1989 | European Pat. Off. . |
| 0340905 | 11/1989 | European Pat. Off. . |
| 812366 | 4/1989 | United Kingdom . |

OTHER PUBLICATIONS

Akimoto et al.; Chemical Abstracts, vol. 115, entry 15916400 (1991).
Akimoto et al, Chemical Abstracts, vol. 118, entry 213101 (1993).
Ootsu et al, Chemical Abstracts, vol. 119, entry 86017 (1993).
Chemical Berichte, vol. 110, 1977, pp. 1462–1469.
Chemical Abstracts, vol. 112, No. 11, Mar. 12, 1990, p. 815, 99168b.
"Advanced Organic Chemistry" by Mar. pp. 796–797 (1985) Published by John Wiley and Sons.
"Rodds Chemistry of Carbon Compounds" Edited by Coffey, vol. IV, Part A, pp. 329–333, 400–403 (1973).
"The Chemistry of the Carbonyl Group", vol. 2 (1970) Interscience Publishers, pp. 19–20.

*Primary Examiner*—John M. Ford
*Attorney, Agent, or Firm*—Foley & Lardner

[57] ABSTRACT

There is provided an improved process for producing novel compounds represented by the general formula:

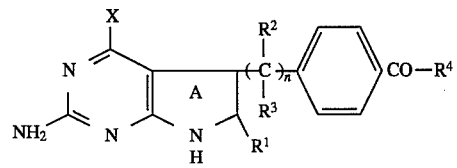

wherein the ring Ⓐ represents a pyrrole ring which may be hydrogenated; X represents an amino, hydroxyl or mercapto group; $R^1$, $R^2$ and $R^3$ each, being the same as or different from the other, represents hydrogen or an alkyl, alkenyl or alkynyl group which may be substituted; $R^4$ represents $OR^5$ wherein $R^5$ represents hydrogen or a hydrocarbon group which may be substituted or $NHCH(COOR^6)CH_2CH_2COOR^7$ wherein $R^6$ and $R^7$ each represents hydrogen or a hydrocarbon group which may be substituted; and n represents an integer of 1 to 4, or a salt thereof from compounds represented by the general formula:

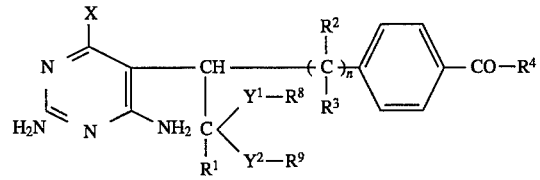

wherein X, $R^1$, $R^2$, $R^3$, $R^4$ and n are the same as defined above; $Y^1$ and $Y^2$ each represents oxygen or sulfur atom; $R^8$ and $R^9$ each, being the same as or different from the other, represents a hydrocarbon group which may be substituted, or salts thereof by an intramolecular ring closure reaction to form a pyrrolopyrimidine ring and, if necessary, reducing pyrrole ring thus formed to pyrroline ring. The compounds are useful as antitumor agents.

13 Claims, No Drawings

PRODUCTION OF PYRROLOPYRIMIDINES AND INTERMEDIATES THEREFOR

This application is a division of Ser. No. 08/029,310, filed Mar. 8, 1993, now U.S. Pat. No. 5,349,064, which is a continuation of application Ser. No. 07/537,807, filed Jun. 14, 1990, now abandoned.

This invention relates to a process for producing novel pyrrolo[2,3-d]pyrimidine derivatives which are useful as an antitumor agent, novel intermediates and production method of the derivatives.

Folic acid, acting as a transferring agent of one-carbon (C1) units derived from formic acid, formaldehyde, etc. in living bodies, plays a role as a coenzyme in various enzymic reaction systems, such as nucleic acid biosynthesis, amino acid peptide metabolism and methane formation systems. In the nucleic acid biosynthesis system, particularly, the compound is essential for the formylation reaction in the two biosynthetic pathways for nucleic acids, i.e. the purine nucleotide pathway and thymidine nucleotide pathway. In order to demonstrate its biological activities, folic acid must ordinarily undergo reduction in two steps to be converted into the active coenzyme form. Amethopterin (methotrexate: MTX) and its analogous compounds are known as drugs that bind strongly to the enzyme (dihydrofolate reductase) controlling its second stage and thus suppress reduction of dihydrofolic acid to tetrahydrofolic acid. These drugs, which act to impair the DNA synthesis, resulting in cell death, have been developed as an antitumor agent and currently occupy the important position established as a clinical agent. On the other hand, there has been reported a novel tetrahydroaminopterine antitumor agent (5,10-dideaza-5,6,7,8-tetrahydroaminopterine: DDATHF), which possesses the basic skeleton of the pteridine ring but unlike the mechanism of action of such structurally analogous drugs, does not exhibit inhibitory activity against dihydrofolate reductase and acts mainly through the mechanism of inhibiting glycineamide.ribonucleotide.transformylase being involved in the initial stage of the purine biosynthesis pathway (Journal of Medicinal Chemistry 28, 914 (1985)).

MTX, an antitumor agent that acts principally through the mechanism as a folic acid antagonist, has long been put in frequent use conventionally as a clinical agent. Nevertheless, it, because of its relatively strong toxicity and inferior efficacy against solid tumors, has failed to achieve satisfactory therapeutic effects. In addition, it has been encountered with the always more serious problem of acquired resistance of tumor cells to the drug. To be particularly expected at present is the development of antitumor drug substances which can demonstrate improved efficacy and enhanced selective toxicity against cancer cells on the basis of new action mechanism. The present inventors, in view of the above circumstances, have conducted repeated extensive research on the process for producing non-pteridine ring compounds as well as the antitumor activity of such compounds. As a result, the present inventors established novel processes for producing 5-substituted pyrrolo [2,3-d]pyrimidine derivatives, which is industrially advantageous in yield, selectivity in pyrrole-ring formation, etc., and also found that a variety of novel compounds prouduced by such production process can exhibit potent growth-inhibitory activity against human tumor cells. On the basis of the foregoing, this invention has been established.

Thus, this invention is directed to:

(1) A process for producing a compound represented by the general formula:

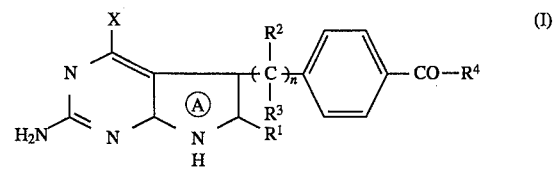

wherein the ring Ⓐ represents a pyrrole ring which may be hydrogenated; X represents an amino, hydroxyl or mercapto group; $R^1$, $R^2$ and $R^3$ each, being the same as or different from the other, represents hydrogen or an alkyl, alkenyl or alkynyl group which may be substituted; $R^4$ represents $OR^5$ (wherein $R^5$ represents hydrogen or a hydrocarbon group which may be substituted) or $NHCH(COOR^6)CH_2CH_2COOR^7$ (wherein $R^6$ and $R^7$ each represents hydrogen or a hydrocarbon group which may be substituted); and n represents an integer of 1 to 4, or a salt thereof characterized in that the said process comprises allowing a compound represented by the general formula:

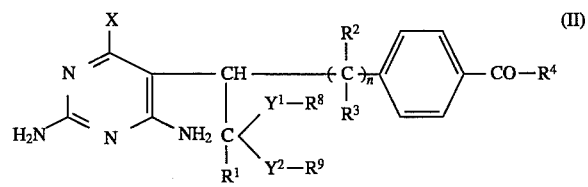

wherein X, $R^1$, $R^2$, $R^3$, $R^4$ and n are the same as defined above; $Y^1$ and $Y^2$ each represents oxygen or sulfur atom; $R^8$ and $R^9$ each, being the same as or different from the other, represents a hydrocarbon group which may be substituted, or a salt thereof to undergo a ring-closure reaction in the course or after regeneration of the group

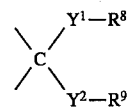

in the compound to a carbonyl group to thereby form the pyrrolo[2,3-d]pyrimidine ring, and, furthermore, if necessary, reducing the pyrrole ring of ring Ⓐ into pyrroline ring, or/and converting $OR^5$ of $R^4$ where $R^5$ is the same as defined above into $NHCH(COOR^6)CH_2CH_2COOR^7$ where $R^6$ and $R^7$ are the same as defined above, (2) Compounds (II) as described in the preceding item (1);

(3) A process as described in preceding item (1) for producing a compound represented by the general formula:

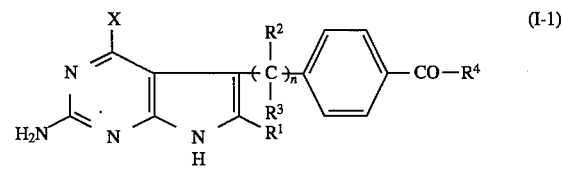

wherein X is an amino, hydroxyl or mercapto group; $R^1$, $R^2$ and $R^3$ each, being the same as or different from the other, represents hydrogen, or an alkyl, alkenyl or alkynyl group which may be substituted; $R^4$ is $OR^5$ wherein $R^5$ represents hydrogen or a hydrocarbon group which may be substituted or $NHCH(COOR^6)CH_2CH_2COOR^7$ wherein $R^6$ and $R^7$ each represents hydrogen or a hydrocarbon group which may be substituted; and n is an integer of 1 to 4 or a salt thereof characterized in that the said process comprises (i) catalytically reducing a compound of the general formula,

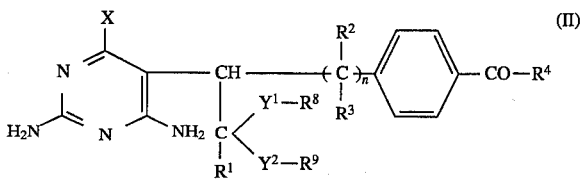

wherein X, $R^1$, $R^2$, $R^3$, $R^4$ and n are the same as defined above; $R^8$ and $R^9$ each, being the same as or different from the other, represents a hydrocarbon group which may be substituted; and $Y^1$ and $Y^2$ each represents oxygen or sulfur atom, or a salt thereof, (ii) contacting the said compound or a salt thereof with an acid or a metal salt, or (iii) reacting the said compound or a salt thereof with an oxidizing agent; and, (4) A process for producing a compound represented by the general formula,

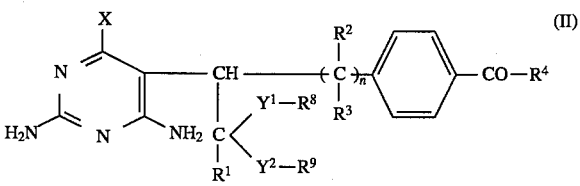

wherein X represents an amino, hydroxyl or mercapto group; $R^1$, $R^2$ and $R^3$ each, being the same as or different from the other, represents hydrogen, or an alkyl, alkenyl or alkynyl group which may be substituted; $R^4$ represents $OR^5$ where $R^5$ represents hydrogen or a hydrocarbon group which may be substituted or $NHCH(COOR^6)CH_2CH_2COOR^7$ wherein $R^6$ and $R^7$ each represents hydrogen or a hydrocarbon group which may be substituted; n represents an integer of 1 to 4, $R^8$ and $R^9$ each, being the same as or different from the other, represents a hydrocarbon group which may be substituted; and $Y^1$ and $Y^2$ each represents oxygen or sulfur atom, or a salt thereof, characterized in that the said process comprises reacting a compound of the formula,

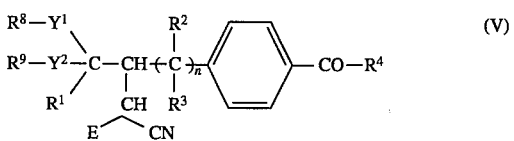

wherein E represents CN, $COOR^{10}$, $CSOR^{10}$ or $CSSR^{10}$ wherein $R^{10}$ represents a hydrocarbon group which may be substituted; and other symbols are the same as defined above, with guanidine or its salt.

The compounds (I) and (II) of the above general formulae where X is a hydroxy or mercapto group can exist in the form of the equilibrium mixture with their tautomers. Given below are the structural formulae of the moiety which are susceptible to tautomerism in relation to X, with the equilibrium relationship between them being shown, as well.

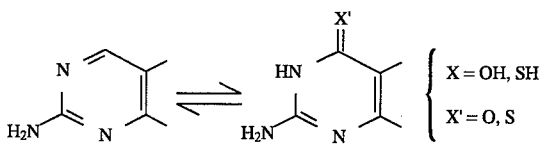

For the convenience of representation, the hydroxy and mercapto forms are described throughout this specification and the corresponding system of nomenclature is adopted, however, it is to be understood that, in both cases, the oxo and thioxo isomers, or tautomers, are included as well.

Although a plurality of asymmetric molecules can exist in the compounds (I) and (II) of this invention, the absolute configurations of such asymmetric centers may be the S- or R-form or a mixture of the R- and S-forms, except the asymmetric carbon atom in the side chain derived from glutamic acid represented by $R^4$ has the absolute configuration of S(L). In this case, a plurality of diastereomers exist, and can be easily separated by the conventional separation and purification means, if necessary. The above described diastereomers, which can be separated by such procedures, are all included within the scope of this invention.

Referring to the above formulae, X represents an amino, hydroxyl or mercapto group, and frequently used is the amino group; the alkyl, alkeny or alkynyl group represented by $R^1$, $R^2$ and $R^3$ includes an alkyl group of 1 to 6 carbon atoms (e.g., methyl, ethyl, propyl and iso-propyl groups); alkenyl groups of 2 to 6 carbon atoms (e.g., vinyl, 1-methylvinyl, 1-propenyl, allyl and allenyl groups); and alkynyl groups of 2 to 6 carbon atoms (e.g., ethynyl, 1-propynyl and propargyl groups), respectively, whereby these groups as represented by $R^2$ and $R^3$ may be different individually in the repeating units shown by n.

The preferred examples of $R^1$, $R^2$ and $R^3$ are hydrogen and the like. n represents an integer of 1 to 4 and may preferably represents 2 or 3.

$R^5$ in the $OR^5$ group represented by $R^4$ as well as $R^6$ and $R^7$ in the $NHCH(COOR^6)CH_2CH_2COOR^7$ designate hydrogen or a hydrocarbon group which may be substituted, respectively. As the hydrocarbon group, there may be mentioned, for example, a lower alkyl group of 1 to 5 carbon atoms (e.g., methyl, ethyl, propyl, iso-propyl, n-butyl, iso-butyl, sec-butyl, tert-butyl, n-pentyl, iso-pentyl, sec-pentyl, neopentyl and tert-pentyl groups) and benzyl or phenyl groups. The preferable examples of $R^4$ include groups represented by the formulas $OR^{5a}$ or $-NHCH(COOR^{6a})CH_2CH_2COOR^{7a}$ (where $R^{5a}$, $R^{6a}$ and $R^{7a}$ each represents, for example, a $C_{1-3}$ alkyl group such as methyl and ethyl, or benzyl group) and the like.

$Y^1$ and $Y^2$, each being the same as or different from the other, represents oxygen or sulfur and both desirably designate oxygen. The hydrocarbon group represented by $R^8$ or $R^9$ includes a lower alkyl of 1 to 5 carbon atoms, benzyl or phenyl group as described in detail for $R^5$, $R^6$ and $R^7$, and among them, frequently used is a $C_{1-3}$ alkyl group such as methyl and ethyl.

Alkyl, alkenyl and alkynyl groups represented by the above $R^1$, $R^2$ and $R^3$ as well as hydrocarbon groups represented by $R^5$, $R^6$, $R^7$, $R^8$ and $R^9$ may have 1 to 3 substituents. Such substituents include, for example, halogen atoms (e.g., fluorine, chlorine, bromine and iodine), nitro group, cyano group, alkoxy groups of about 1 to 4 carbon atoms (e.g., methoxy, ethoxy, propoxy, iso-propoxy, n-butoxy, iso-butoxy, sec-butoxy and tert-butoxy groups), alkanoyl groups of about 1 to 4 carbon atoms (e.g., formyl, acetyl, propionyl, n-butyryl and iso-butyryl groups), alkanoyloxy groups of about 1 to 4 carbon atoms (e.g., formyloxy, acetyloxy, propionyloxy, n-butyryloxy and iso-butyryloxy groups), alkoxycarbonyl groups of about 2 to 4 cabon atoms (e.g., methoxycarbonyl, ethoxycarbonyl, n-propoxycarbonyl, iso-propoxycarbonyl, n-butoxycarbonyl, iso-butoxycarbonyl and tert-butoxycarbonyl groups), trifluoromethyl group, alkylthio groups of about 1 to 4 carbon atoms (e.g., methylthio, ethylthio, propylthio, isopropylthio, n-butylthio, sec-butylthio and tert-butylthio groups), alkylsulfinyl groups of about 1 to 4 cabon atoms (e.g., methylsulfinyl, ethylsulfinyl, propylsulfinyl and butylsulfinyl groups), alkylsulfonyl groups of about 1 to 4 carbon atoms (e.g., methylsulfonyl, ethylsulfonyl, propylsulfonyl and butylsulfonyl groups) and the like. In the case that $R^5$, $R^6$, $R^7$, $R^8$ or $R^9$ is benzyl or phenyl group, it may be substituted by alkyl groups of 1 to 4 carbon atoms (e.g., methyl, ethyl, propyl, isopropyl, butyl, isobutyl, sec-butyl and tert-butyl groups), alkenyl groups of 1 to 3 carbon atoms (e.g., methylene, vinyl, 1-methylvinyl, 1-propenyl, allyl and allenyl groups), alkynyl groups of 2 to 3 carbon atoms (e.g., ethynyl, 1-propynyl and propargyl groups) and the like.

Given in the following is a detailed description of the process for producing the compounds (I) or their salts of this invention.

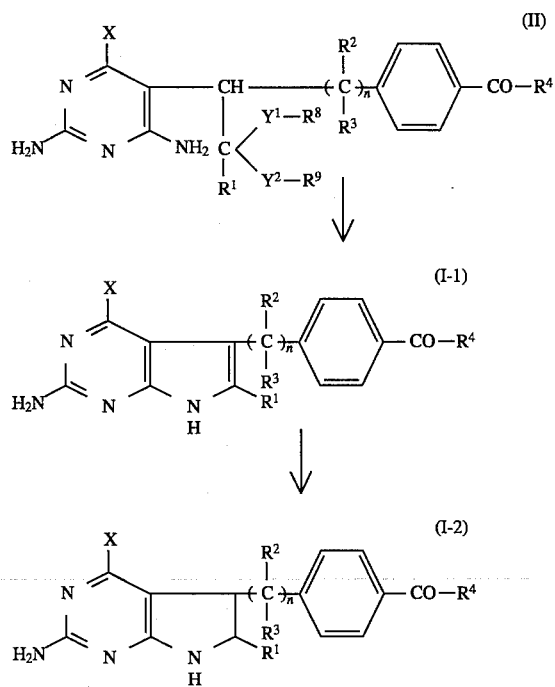

In the steps of producing the compounds (I) or their salts of this invention, the reaction of regenerating the group

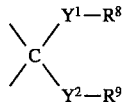

in the compounds (II) or their salts to the caronyl group (>C=O) can be carried out by allowing the compound (II) or its salt to undergo a decomposition reaction, as such or in the presence of a suitable reaction solvent, at a reaction temperature in the range of about −40° C. to the boiling point (up to about 150° C.) of such reaction solvent, preferably about −10° C. to 75° C. for a length of time of about 10 minutes to 100 hours, preferably about 30 minutes to 24 hours. As the said decomposition reaction, there may be mentioned, for example, the catalytic reduction reaction (Method A), hydrolysis reaction under acidic conditions (Method B-1) or decomposition reaction under acidic, non-aqueous conditions (Method B-2), and decomposition reaction making use of metal salt (Method C-1) or decomposition reaction making use of oxidizing agent (Method C-2), and particularly preferable is Method B-1 or B-2.

The amount of catalyst employed in Method A is usually about 0.005 to 2.0 moles, preferably about 0.01 to 0.5 mole to 1 mole of the compound to be reduced. As the catalyst, there may be utilized palladium, platinum, rhodium, Raney nickel and the like, whereby the addition of trace amounts of acid (e.g., acetic acid, trifluoroacetic acid, hydrochloric acid, sulfuric acid, etc.) also permits the reaction to proceed favorably. The amount of the acid used in Method B-1 is usually about 0.01 to 100 moles, preferably about 0.1 to 10 moles to 1 mole of the compound to be hydrolyzed, and the examples of the acid include mineral acids, such as hydrochloric acid, hydrobromic acid, sulfuric acid, nitric acid and phosphoric acid; and organic acids, such as trifluoroacetic acid, trichloroacetic acid, methanesulfonic acid, benzenesulfonic acid, p-toluenesulfonic acid and camphorsulfonic acid, etc., and, in particular, a mineral acid such as hydrochloric acid, etc. is frequently used.

The amount of the acid used in Method B-2 is usually about 0.01 to 10 moles, preferably about 0.1 to 2 moles to 1 mole of the compound to be decomposed, and the examples of the acid are mineral acids, such as hydrogen chloride, hydrogen bromide, perchloric acid, sulfuric acid, nitric acid, phosphoric acid, etc.; organic acids, such as trifluoroacetic acid, trichloroacetic acid, methanesulfonic acid, benzenesulfonic acid, p-toluenesulfonic acid, camphorsulfonic acid, etc.; and Lewis acids, such as anhydrous zinc chloride, anhydrous aluminum chloride ($AlCl_3$), anhydrous ferric chloride, titanium tetrachloride ($TiCl_4$), tin tetrachloride ($SnCl_4$), antimony pentachloride, cobalt chloride, cupric chloride, boron trifluoride-diethyl ether, etc.

The amount of metal salts used in Method C-1 is usually about 0.1 to 10 equivalents, preferably about 0.5 to 2 equivalents to 1 mole of the compound to be decomposed, and the examples of the metal salts include cupric chloride, silver nitrate, silver oxide, mercuric chloride, tellurium salts (e.g., tellurium nitrate, tellurium trifluoroacetate,), etc.

The amount of oxidizing agents used in Method C-2 is usually about 0.25 to 10 equivalents, preferably 0.25 to 2 equivalents to the compound to be oxidized, and the examples of the oxidizing agents include oxygen-light, hydrogen peroxide, perbenzoic acid, m-chloroperbenzoic acid, perchlorates (lithium perchlorate, silver perchlorate, mercuric perchlorate, tetrabutylammonium perchlorate, etc.), nitrosylsulfuric acid, alkylnitrite acid (e.g., isoamyl nitrite, etc.), iodine, bromine, chlorine, N-bromosuccinimide, sulfuryl chloride, chloramine T, etc.

Referring to the reaction solvent, usable in Methods A and B-1 are, for example, water, alcohols (e.g., methanol, ethanol, propanol, iso-propanol, butyl alcohol, sec-butyl alcohol, tert-butyl alcohol, ethylene glycol, methoxyethanol, ethoxyethanol), acetic acid esters (e.g., methyl acetate, ethyl acetate), ethers (e.g., dimethyl ether, diethyl ether, tetrahydrofurane, dioxane, monoglyme, diglyme), aromatic hydrocarbons (e.g., benzene, toluene, xylene), ketones (e.g. acetone), nitriles (e.g., acetonitrile), pyridine, amides (e.g., dimethylformamide, dimethylacetamide), sulfoxides (e.g., dimethylsulfoxide), sulfolane and suitable solvent mixture thereof: In the case of Method A, preferably used is methanol, ethanol, ethyl acetate, tetrahydrofuran, dioxane or benzene, and in the case of Method B-1, there is frequently used a water-containing organic solvent wherein 0.01 to 100 g, preferably 0.1 to 10 g of a hydrophilic solvent, preferably an alcohol such as methanol, ethanol, etc., an acetic acid ester such as ethyl acetate, an ether such as tetrahydrofuran, dioxane, etc., a ketone such as acetone, etc., or a nitrile such as acetonitrile, etc. is contained together with 1 g of water.

These solvents are employed in an amount of usually 1.0 to 2,000 ml, preferably 5.0 to 100 ml to 1 g of the compound (II) or its salt.

In the case of Method B-2, there may be utilized, for example, acetic acid esters (e.g., methyl acetate, ethyl acetate), ethers (e.g., diemthyl ether, diethyl ether, tetrahydrofurane, dioxane, monoglyme, diglyme), aromatic hydrocarbons (e.g., benzene, toluene, xylene), halogenated hydrocarbons (e.g., dichloromethane, chloroform, carbon tetrachloride), ketones (e.g. acetone), nitriles (e.g. acetonitrile), nitromethane, pyridine, dimethylformamide or suitable solvent mixtures thereof; and preferable solvents are aromatic hydrocarbons such as benzene, toluene, etc., halogenated hydrocarbons such as dichloromethane, chloroform, carbon tetrachloride, etc., or nitriles such as acetonitrile, etc.

In the event of employing Methods C-1 and C-2, there are usable, for example, water, alcohols (e.g., methanol, ethanol, propanol, iso-propanol, butyl alcohol, sec-butyl alcohol, tert-butyl alcohol, ethylene glycol, methoxyethanol, ethoxyethanol), ethers (e.g., dimethyl ether, diethyl ether, tetrahydrofuran, dioxane, monoglyme, diglyme), aromatic hydrocarbons (e.g., benzene, toluene, xylene), halogenated hydrocarbons (e.g., dichloromethane, chloroform, carbon tetrachloride, etc.), acetone, acetonitrile and suitable solvent mixtures thereof. In any of Methods C-1 and C-2, preferable solvents are methanol, ethanol, tetrahydrofuran, dioxane or acetonitrile, and a mixture of thus solvent and water. What method should be applied to regenerate the carbonyl group (>=CO) can suitably be determined depending on the chemical properties, etc. of $—Y^1—R^8$ and $—Y^2—R^9$, and usually Method B-1 is frequently used as more preferable method.

In the intramolecular ring-closure reaction in the steps of producing the compounds (I) or their salts of this invention, during or after regeneration to a carbonyl group (>C=O), usually the carbonyl group condenses spontaneously with the amino group on the pyrimidine ring to thereby form the pyrrolo[2,3-d]pyrimidine ring. Particularly, in Methods B-1 and B-2, the regeneration of the carbonyl group and intermolecular ring-closure reaction proceed rapidly, resulting the advantageous yield of the product. In Methods A, C-1 and C-2, the presence of an acid catalyst permits the ring-closure reaction to proceed quickly and in improved yields. As such a acid catalyst, there can be mentioned the mineral acids, organic acids or Lewis acids as described in detail for Methods B-1 and B-2.

The compound (I-1) thus obtained wherein ring Ⓐ is a pyrrole ring can be easily converted, if necessary, to the compound (I-2) wherein the ring Ⓐ is a pyrroline ring by a catalytic reduction. As the catalytic reduction reaction, Method A as described above can be advantageously applied as such.

The compound (I-1) or (I-2) or their salts wherein $R^4$ is $OR^5$ where $R^5$ is a hydrocarbon group which may be substituted can also be subjected to the socalled ester decomposition or hydrolysis reaction to thereby produce the compound where $R^5$ is hydrogen, followed by conversion to the compound wherein $R^4$ is an $NHCH(COOR^6)CH_2CH_2COOR^7$. The ester decomposition reaction as well as the conversion reaction to the $NHCH(COOR^6)CH_2CH_2COOR^7$ group can be conducted by the per se known procedures [J. F. W. McOmine, "Protective Groups in Organic Chemistry", Plenum Press, London and New York (1973); and M. Fieser and L. Fieser, "Reagents for Organic Synthesis", vols. 1 to 13, Wiley-Interscience, New York, London, Sydney and Toronto (1969–1988)].

In the compounds (I) and (II) or their salts, furthermore, the amino, hydroxyl or mercapto group represented by X each can be converted to the other by the substituent conversion reaction on the pyrimidine ring as known in literature [a separate volume of *Tanpakushitsu Kakusan Kohso* (Protein, Nucleic Acids and Enzymes), "Chemical Synthesis of Nucleic Acids", Kyoritsu Publishing Co. (1968)].

The compound (I) or its salt of this invention produced by the above procedure can be isolated or purified from the reaction mixture by usual means, for example, concentration, extraction with a solvent, chromatography, recrystallization, etc.

The compounds (II) or their salts of this invention, which are utilized as intermediates in the process of this invention can be produced, for example, by the reaction steps as shown in the following.

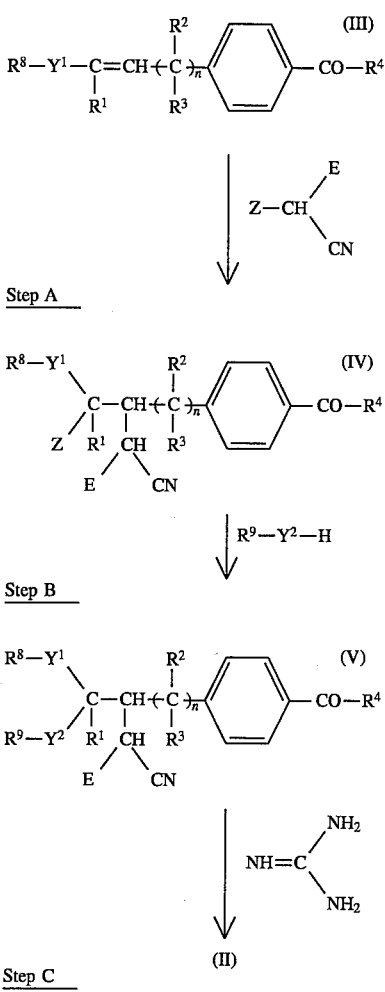

In the above formulae, $Y^1, Y^2, R^1, R^2, R^3, R^4, R^8, R^9$ and n are as defined above. E represents an CN group or $COOR^{10}$, $CSOR^{10}$ or $CSSR^{10}$ (wherein $R^{10}$ is a hydrocarbon group which may be substituted, while Z is a halogen atom (e.g., chlorine, bromine, iodine)). As $R^{10}$ in the $COOR^{10}$, $CSOR^{10}$ or $CSSR^{10}$ group, there may be mentioned, for example, the hydrocarbon groups which may be substituted as described in detail for $R^5$ to $R^9$, and preferable groups are $C_{1-4}$ alkyl groups such as methyl and ethyl groups, etc. or benzyl group etc. The above reaction steps are described in detail in the following;

Step A:

The step involves a step of allowing

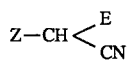

to add to the double bond ($R^8$—$Y^1$—C=CH—) of the compound (III) to produce the compound (IV). The amount of

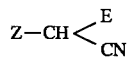

to be used against the compound (III) usually ranges from about 0.5 to 4 mole equivalents, preferably from about 0.8 to 1.5 mole equivalents. This reaction can be carried out, in the presence of a suitable solvent, at a reaction temperature in the range of about −10° C. to the boiling point (up to about 150° C.) of the reaction solvent used, preferably about 0° C. to 100° C., for about 30 minutes to 48 hours. The solvent to be utilized in the reaction includes, for example, alcohols (e.g., methanol, ethanol), ethers (e.g., dimethyl ether, diethyl ether, tetrahydrofuran, dioxane, monoglyme, diglyme), nitriles (e.g., acetonitrile), esters (e.g., ethyl acetate), halogenated hydrocarbons (e.g., dichloromethane, chloroform, carbon tetrachloride), aromatic hydrocarbons (e.g., benzene, toluene, xylene) or suitable sovlent mixtures thereof. In carrying out the reaction, exposure of light or addition of organic peroxides can also permit the reaction to proceed more advantageously. The said organic peroxides inlcude, for example, t-butyl hydroperoxide, peracetic acid, perbenzoic acid, m-chloroperbenzoic acid, etc. The compound (IV) obtained by such procedure is relatively reactive, and may be isolated at this stage by usual means as described above, but can also be utilized in the subsequent step directly without being isolated.

Step B:

The compound (IV) obtained in the step A can be reacted with alcohols or thiols represented by $R^9$—$Y^2$—H in the presence of a suitable solvent at a reaction temperature in the region of about −10° C. to the boiling point (up to about 100° C.) of the reaction solvent, preferably about 0° c. to 50° C., for about 10 minutes to 24 hours to be converted to the compound (V). As the solvent to be used in the reaction, there may be used, for example, ethers (e.g., dimethyl ether, diethyl ether, tetrahydrofuran, dioxane, monoglyme, diglyme), nitriles (e.g., acetonitrile), esters (e.g., ethyl acetate), halogenated hydrocarbons (e.g., dichloromethane, chloroform, carbon tetrachloride), aromatic hydrocarbons (e.g., benzene, toluene, xylene, etc.) or suitable solvent mixtures thereof. In addition, the alcohols or thiols themselves as represented by $R^9$—$Y^2$—H may be utilized in excess as the solvent. The compound (V) thus obtained may be isolated from the reaction mixture by usual means as described above, but the reaction mixture as it is may be utilized as a raw material in the next step.

Step C:

The compound (V), upon treatment with guanidine or its salt (e.g., a salt with an acid as described in the above Method B-1, etc.) in a suitable solvent, undergoes reaction with its cyano, ester or thioester group and gives rise to cyclization simultaneously to form a pyrimidine ring, thereby yielding the compound (II) or its salt of this invention. This reaction proceeds at a reaction temperature of 0° to 150° C., preferably 20° to 100° C., for a reaction time in the range of 1 to 48 hours. The reaction, when conducted under basic conditions, can also be allowed to proceed advantageously. The base used for making the conditions, includes, for example, metal alkoxides, such as sodium methoxide, sodium ethoxide, potassium tert-butoxide, etc. As the reaction solvent, there may be used, for example, methanol, ethanol, propanol, tert-butyl alcohol, dimethyl sulfoxide, hexamethylphosphoramide or suitable solvent mixtures thereof, etc.

The compound (II) of this invention as well as the starting or intermediate compounds (III) to (V) as produced in these steps can be isolated or purified from the corresponding reaction mixtures by use of conventional separation and purification means, such as concentration, solvent extraction, chromatography, recrystallization, etc.

The compound (I) and the compound (II) obtained by the production process according to this invention or an intermediate thereof, may be in the form of salts, preferably pharmaceutically acceptable salts. As the base salts, there may be mentioned, for example, salts with alkali metals, alkaline earth metals, non-toxic metals, ammonium and substituted ammoniums, such as sodium, potassium, lithium, calcium, magnesium, aluminum, zinc, ammonium, trimethyl ammonium, triethyl ammonium, triethanol ammonium, pyridinium or pyridinium substituted with, e.g., carbamoyl group or halogen such as chlorine, bromine, etc. The acid salts include, for example, salts with mineral acids, such as hydrochloric acid, sulfuric acid, nitric acid, phosphoric acid and boric acid, and organic acids, such as oxalic acid, tartaric acid, acetic acid, trifluoroacetic acid, methanesulfonic acid, benzenesulfonic acid, p-toluenesulfonic acid and camphorsulfonic acid, and the like.

The compounds (I) or their salts exhibit excellent antitumor activity against mice tumor cell lines (P388, L1210, L5178Y, B16 melanoma, MethA, Lewis Lung Carcinoma, S180 sarcoma, Ehrlich Carcinoma and Colon 38) and human tumor cell lines (HL60 and KB), while at the same time, they possesse reductive activity against tumors (e.g., melanoma, sarcoma, mastocytoma, carcinoma, neoplasia, etc.) attacking warm-blooded animals and also life-span extending activity against warm-blooded animals having suffered from tumors. Consequently, the pharmaceutical preparations which contain the compounds (I) or their salts can be used as a safe antitumor agent intended for the treatment of tumors in warm-blooded animals, particualrly mammals (e.g., mice, rats, cats, dogs, rabbits, etc.).

In the case of being utilized as an antitumor agent, the compound (I) or its salt can be administered orally or parenterally as such or after being processed into various dosage forms, such as powders, granules, tablets, capsules, suppositories and injections, by means of the conventionally employed procedures with use of pharmacologically allowable carriers, excipients, diluents, etc. Although the dosage amounts vary depending upon the species of animals to be treated, kind of diseases, symptoms, type of compounds, route of administration and the like, the compound (I) or its salt may be administered to the above-described warm-blooded animals, for example, in the case of oral administration, at daily doses in the range of about 2.0 to 200 mg/kg body weight, preferably 5.0 to 100 mg/kg body weight, or, in the case of parenteral administration, at daily doses in the range of about 1.0 to 100 mg/kg body weight, preferably 2.5 to 50 mg/kg body weight. As the method of administration by injections, there may be mentioned intramuscular injection, intraperitoneal injection, subcutaneous injection, intravenous injection and the like.

The above-mentioned procedure of processing into dosage forms can be carried out following the per se known methods. The above preparations for oral administration, for example, tablets, can be prepared by suitably incorporating binders (e.g., hydroxypropyl cellulose, hydroxypropyl methycellulose, macrogoal, etc.), disintegrating agents (e.g., starch, carboxymethyl cellulose calcium, etc.), lubricating agents (e.g., magnesium stearate, talc, etc.) and the like.

The preparations for parenteral administration, for example, injectable solutions, can be produced by suitably incorporating tonicity agents (e.g., glucose, D-sorbitol, D-mannitol, sodium chloride, etc.), preservatives (e.g., benzyl alcohol, chlorobutanol, methyl p-oxybenzoate, propyl p-oxybenzoate, etc.), buffers (e.g., phosphate buffer, sodium acetate buffer, etc.) and the like.

By way of specific example of preparing tablets, on the basis of amounts per tablet, about 1.0 to 25 mg of the compound (I) of this invention or its salt, 100 to 500 mg of lactose, about 50 to 100 mg of corn starch and about 5 to 20 mg of hydroxypropyl cellulose are mixed by means of the conventional procedure, and the mixture is granulated, followed by mixing with corn starch and magnesium stearate and compressing into a tablet weighing about 100 to 500 mg and measuring about 3 to 10 mm in diameter. Such tablets produced can be provided with coating by use of an acetone-ethanol mixed solution having hydroxypropylmethyl methylcellulose (about 10 to 20 mg) and castor oil (about 0.5 to 2 mg) dissolved at a concentration of about 5 to 10% (the amounts are on the basis of amounts per tablet) to thereby produce enteric coated tablets.

By way of specific example of preparing injectable solutions, on the basis of amounts used per ampoule, for example, a solution of about 2.0 to 50 mg of sodium salt of the compound (I) of this invention in about 2 ml of isotonic saline, is filled into an ampoule, which is then fused and heat-sterilized at about 110° C. for about 30 minutes, or about 2.0 to 50 mg of the said sodium salt is dissolved in a solution of about 10 to 40 mg of mannitol or sorbitol in about 2 ml of sterilized distilled water, and the resulting solution is filled into an ampoule, followed by lyophilizing and fusing to produce the injections. On the occasion of use, the seal of the lyophilized preparation is opened, and the active compound is dissolved, for example, with physiological saline so as to make a solution having the compound in a concentration of about 1.0 to 25 mg/ml, thereby an injectable solution intended for subcutaneous, intravenous or intramuscular administration is provided.

As is described above, the production process of this invention starts with cheap and industrially available raw materials and can provide antitumor agents being highly useful as a drug in shortened steps and in increased yields. In addition, the process is practically simplified and facilitated in terms of reaction processability and workability, and is more favored from the standpoint of the production facilities, thus providing an industrially advantageous process for producing 5-substituted pyrrolo[2,3d] pyrimidine derivatives.

Described below are the reference examples and examples to illustrate this invention specifically.

REFERENCE EXAMPLE 1

Production of tert-butyl 4-(4-methoxy-3-butenyl)benzoate

A 1.0 mole tetrahydrofuran solution (11.0 ml) of potassium tert-butoxide was added to a toluene solution (12 ml) of (methoxymethyl)triphenylphosphonium chloride (3.77 g) at 0° C., and after stirring for 10 minutes, a toluene solution (10 ml) of tert-butyl 4-(3-oxopropyl)benzoate (2.34 g) was added dropwise to the mixture at the same temperature, followed by stirring at 0° C. for 20 minutes. The reaction solution was admixed with ether (40 ml), and the organic layer was separated, then washed successively with water and saturated aqueous solution of sodium chloride, and dried over anhydrous sodium sulfate. The solvent was distilled off under reduced pressure, and the thus obtained residue was treated with hexane, followed by filtering out the resultant triphenylphosphine oxide. The filtrate was concentrated under reduced pressure, and the residue was purified by column chromatography (80 g of silica gel; ether-hexane= 20:1) to give the subject compound (1.92 g).

IR (neat): 2980, 2945, 1715, 1655, 1610, 850 cm$^{-1}$.

$^1$H-NMR (CDCl$_3$) : 1.59(9H,s), 2.24(1.2H,td,J=8 Hz,7 Hz), 2.39(0.8H,td,J=8 Hz,7 Hz), 3.48(1.8H,s), 3.56(1.2H,s), 4.33(0.4H,td,J=7 Hz,6 Hz), 4.71(0.6H,dt,J=13 Hz,7 Hz), 5.88(0.4H,d,J=6 Hz), 6.28(0.6H,d,J=13 Hz), 7.21(2H,d,J=8 Hz), 7.91(2H,d,J=8 Hz).

REFERENCE EXAMPLE 2

Production of tert-butyl 4-[4,4-dicyano-3-(dimethoxymethyl)butyl] benzoate

Under argon atmosphere, bromomalononitrile (1.27 g) and the compound (1.91 g) as obtained in Reference Example 1 were dissolved in dichloromethane (66 ml), and after addition of molecular sieve (3A, 1.0 g), the reaction mixture was irradiated with ultraviolet rays for 2 hours by use of a ultraviolet lamp for analytical use having the cover removed. Methanol (4 ml) was added to the reaction mixture, which was stirred for 10 minutes and poured into ice water containing 2N aqueous potassium carbonate solution (5 ml), followed by extraction with dichloromethane. The organic layer was washed with water and dried over anhydrous sodium sulfate. The solvent was distilled off under reduced pressure, and the resulting residue was purified by column chromatography (75 g of silica gel; ethyl acetate-hexane=1:10) to give the subject compound (2.08 g) in the form of a colorless oily substance.

IR (Neat): 2980, 2945, 2840, 2250, 1710, 1606, 845 cm$^{-1}$.

$^1$H-NMR (CDCl$_3$): 1.60(9H,s), 1.90–2.20(2H,m), 2.20–2.32(1H,m), 2.89(2H,t,J=8 Hz), 3.39(3H,s), 3.46(3H, s), 4.13(1H,d,J=4 Hz), 4.36(1H,d,J=5 Hz), 7.28(2H,d,J=8 Hz), 7.95(2H,d,J=8 Hz).

REFERENCE EXAMPLE 3

Production of tert-butyl 4-(5-methoxy-4-pentenyl)benzoate

By following the same procedure as described in Reference Example 1, tert-butyl 4-(4-oxobutyl)benzoate (993 mg) was treated with (methoxymethyl)triphenylphosphonium chloride to give the subject compound (918 mg) in the form of a colorless oily substance.

IR (Neat): 2980, 2940, 2860, 1710, 1660, 1603, 860, 845 cm$^{-1}$.

$^1$H-NMR (CDCl$_3$): 1.55–1.76(2H,m), 1.59(9H,s), 1.96(0.6H,dt,J=7 Hz,7 Hz), 2.10(0.4H,tdd,J=7 Hz,7 Hz,7 Hz), 2.66(2H,t,J=8 Hz), 3.51(1.8H,s), 3.59(1.2H,s), 4.35(0.4H,td,J=7 Hz,6 Hz), 4.73(0.6H,dt,J=13 Hz,7 Hz), 5.91(0.4H,dt,J=6 Hz,1 Hz), 6.29(0.6H,d,J=13 Hz), 7.21(2H, d,J=8 Hz), 7.89(0.8H,d,J=8 Hz), 7.90(1.2H,d,J=8 Hz).

REFERENCE EXAMPLE 4

Production of tert-butyl 4-[5,5-dicyano-4-(dimethoxymethyl)pentyl] benzoate

By following the same procedure as described in Reference Example 2, the compound (276 mg) as obtained in Reference Example 3 was reacted with bromomalononitrile to give the subject compound (202 mg) in the form of a colorless oily substance.

IR (Neat): 2975, 2930, 2245, 1710, 1605, 860, 845 cm$^{-1}$.

$^1$H-NMR (CDCl$_3$): 1.59(9H,s), 1.60–1.92(4H,m), 2.20–2.30(1H,m), 2.73(2H,t,J=7 Hz), 3.40(3H,s), 3.45(3H, s), 4.11(1H,d,J=4 Hz), 4.31(1H,d,J=5 Hz), 7.24(2H,d,J=8 Hz), 7.93(2H,d,J=8 Hz).

REFERENCE EXAMPLE 5

Production of tert-butyl 4-(6-methoxy-5-hexenyl)benzoate

By following the same procedure as described in Reference Example 1, tert-butyl 4-(5-oxobutyl)benzoate (476 mg) was treated with (methoxymethyl)triphenylphosphonium chloride to give the subject compound (430 mg) in the form of a colorless oily substance.

IR (neat): 2940, 1715, 1650, 1605, 1455, 850 cm$^{-1}$.

$^1$H-NMR (CDCl$_3$): 1.32–1.44(2H,m), 1.59(9H,s), 1.52–1.70(2H,m), 1.94(1.2H,td,J=8 Hz,7 Hz), 2.09(0.8H,td,J=8 Hz,7 Hz), 2.65(2H,t,J=8 Hz), 3.49(1.8H,s), 3.58(1.2H,s), 4.31(0.4H,td,J=7 Hz,6 Hz), 4.70(0.6H,dt,J=13 Hz,7 Hz), 5.88(0.4H,d,J=6 Hz), 6.28(0.6H,d,J=13 Hz), 7.21(2H,d,J=8 Hz), 7.90(2H,d,J=8 Hz).

REFERENCE EXAMPLE 6

Production of tert-butyl 4-[6,6-dicyano-5-(dimethoxymethyl)hexyl] benzoate

By following the same procedure as described in Reference Example 2, the compound (420 mg) as obtained in Reference Example 5 was reacted with bromomalononitrile to give the subject compound (432 mg) in the form of a colorless oily substance.

IR (Neat): 2940, 2250, 1715, 1610, 1455, 845 cm$^{-1}$.

$^1$H-NMR (CDCl$_3$): 1.48–1.81(6H,m), 1.59(9H,s), 2.18–2.28(1H,m), 2.71(2H,t,J=7 Hz), 3.40(3H,s), 3.46(3H, s), 4.10(1H,d,J=4 Hz), 4.31(1H,d,J=5 Hz), 7.23(2H,d,J=8 Hz), 7.92(2H,d,J=8 Hz).

EXAMPLE 1

Production of tert-butyl 4-[3-(2,4,6-triamino-pyrimidin-5-yl)-4,4-dimethoxybutyl]benzoate Under argon atmosphere, a tert-butyl alcohol suspension (30 ml) of guanidine hydrochloride (640 mg) was admixed with a tetrahydrofuran solution (6.70 ml) of 1.0 mole of potassium tert-butoxide, followed by stirring for 10 minutes, and a tert-butyl alcohol solution (10 ml) of the compound (2.00 g) of Reference Example 2 was added to the mixture, followed by heating under reflux for 2 hours. The reaction solution was poured into water (200 ml) containing 1.0N aqueous potassium hydrogensulfate solution (1 ml), followed by extraction with dichloromethane. The organic layer was dried over anhydrous sodium sulfate, and the solvent was distilled off under reduced pressure. The resulting residue was purified by column chromatography (50 g of silica gel; dichloromethane-methanol=30:1→15:1) to give the subject compound (2.17 g) in the form of a colorless amorphous substance.

IR (KBr): 3475, 3360, 3200, 2975, 2930, 1710, 1607, 1563, 1430, 843, 800 cm$^{-1}$.

$^1$H-NMR (CDCl$_3$): 1.58(9H,s), 1.86–2.05(1H,m), 2.25–2.53(2H,m), 2.57–2.80(2H,m), 3.45(3H,s), 3.48(3H,s), 4.35(1H,d,J=3 Hz), 4.36(2H,brs), 4.48(2H,brs), 5.21(2H, brs), 7.18(2H,d,J=8 Hz), 7.88(2H,d,J=8 Hz).

EXAMPLE 2

Production of diethyl N-[4-[2-(2,4-diamino-7H-pyrrolo[2,3-d]pyrimidin-5-yl)ethyl]benzoyl]-L-glutamate The compound (200 mg) as obtained in Example 1 was dissolved in trifluoroacetic acid (1 ml) and water (20 mg), followed by stirring at room temperature for 2 hours. The trifluoroacetic acid was distilled off under reduced pressure, followed by drying under vacuum at 70° C., and the resulting residue and diethyl L-glutamate hydrochloride (172 mg) were suspended in dimethylformamide (2 ml). A dimethylformamide solution (2 ml) of diethyl phosphorocyanidate (82 mg) was added to the suspension at 0° C., followed by stirring for 15 minutes, and a dimethylformamide solution (2 ml) of triethylamine (218 mg) was added dropwise to the mixture at the same temperature, followed by stirring at 0° C. for 30 minutes and then at room temperature for 2 hours. The solvent was distilled off under reduced pressure, and the resulting residue was purified by column chromatography (15 g of silica gel; dichloromethaen separated from conc. ammonia→dichloromethane—10% ammoniacal ethanol 40:1→30:1) to give the subject compound (195 mg) in the form of a colorless amorphous substance.

IR (KBr): 3375, 3200, 2980, 2930, 1735, 1640, 1605, 1572 cm$^{-1}$.

$^1$H-NMR (CDCl$_3$): 1.23(3H,t,J=7 Hz), 1.31(3H,t,J=7 Hz), 2.10–2.40(2H,m), 2.48 (2H,dd,J=6 Hz,6 Hz), 3.00(4H,brs), 4.12(2H,q,J=7 Hz), 4.2 5(2H,q,J=7 Hz), 4.61 (2H,brs), 4.75–4.86 (1H,m), 4.95(2H,brs), 6.40(1H,s), 7.13(1H,d,J=7 Hz), 7.22 (2H,d,J=8 Hz), 7.74(2H,d,J=8 Hz), 8.55(1H,brs).

EXAMPLE 3

Production of N-[4-[2-(2,4-diamino-7H-pyrrolo[2,3-d]pyrimidin-5-yl)ethyl]benzoyl]-L-glutamic acid To a tetrahydrofuran-water mixed solution (2:1, 3 ml) of the compound (80 mg) as obtained in Example 2 was added 1.0N aqueous sodium hydroxide solution (0.497 ml), followed by stirring at room temperature for 1 hour. The reaction solution was concentrated to a total volume of 1.0 ml under reduced pressure, and after the resulting insoluble matter was filtered through Millipore filter, the filtrate was cooled at 0° C. and admixed with acetic acid (0.1 ml). The resulting crystals were recovered by filtration, washed thoroughly with ice water and dried at 70° C. under reduced pressure to give the subject compound (61 mg) in the form of white crystals.

IR (KBr): 3320, 1660, 1637, 1540 cm$^{-1}$.

$^1$H-NMR (Me$_2$SO-d$_6$): 1.85–2.20(2H,m), 2.46(2H,t,J=8 Hz), 2.96(4H,brs), 4.30–4.45(1H,m), 5.49(2H,brs), 6.13(2H, s), 6.37(1H,s), 7.33(2H,d,J=8 Hz), 7.80(2H,d,J=8 Hz), 8.46(1H,d,J=7 hz), 10.34(1H,brs).

EXAMPLE 4

Production of tert-buty 4-[4-(2,4,6-triaminopyrimidin-5-yl)-5,5-dimethoxypentyl]benzoate By following the same procedure as described in Example 1, the compound (190 mg) as obtained in Reference Example 4 was reacted with guanidine hydrochloride to give the subject compound (214 mg) in the form of white powder.

IR (KBr): 3480, 3380, 3200, 2980, 2940, 1715, 1610, 1570, 1440, 850, 805 cm$^{-1}$.

$^1$H-NMR (CDCl$_3$): 1.40–1.65(3H,m), 1.59(9H,s), 1.75–2.05(1H,m), 2.62(2H,t,J=7 Hz), 2.81(1H,ddd,J=11 Hz,3 Hz,1 Hz), 3.46(3H,s), 3.50(3H,s), 4.36(1H,d,J=3 Hz), 4.49(4H,brs), 5.16(2H,brs), 7.18(2H,d,J=8 Hz), 7.88(2H,d, J=8 Hz).

EXAMPLE 5

Production of tert-butyl 4-[3-(2,4-diamino-7H-pyrrolo[2,3-d]pyrimidin-5-yl)propyl]benzoate The compound (206 mg) as obtained in Example 4 was dissolved in tetrahydrofuran-water mixed solution (3:1, 8 ml), and 1N hydrochloric acid (4.8 ml) was added to the solution, followed by stirring at room temperature for 18 hours. The reaction solution was admixed with 1N sodium hydroxide solution (4.8 ml) for neutralization, followed by extraction with dichloromethane, and the extract layer was dried over anhydrous sodium sulfate and freed of solvent under reduced pressure. The resulting residue was purified by column chromatography (10 g of silica gel; dichloromethane-methanol=15:1) to give the subject compound (126 mg) in the form of white crystals. m.p. 172°–173° C.

IR (KBr): 3335, 3180, 2975, 2935, 1710, 1607, 1287, 1163, 1110 cm$^{-1}$.

$^1$H-NMR (Me$_2$SO-d$_6$): 1.54 (9H,s), 1.77–1.90(2H,m), 2.68(2H ,t,J=8 Hz), 2.72(2H,t,J=8 Hz), 5.54(2H,brs), 6.11(2H,brs), 6.45(1H,s), 7.33(2H,d,J=8 Hz), 7.82(2H,d,J=8 Hz), 10.51(1 H,s).

EXAMPLE 6

Production of diethyl N-[4-[3-(2,4-diamino-7H-pyrrolo[2,3-d]pyrimidin-5-yl)propyl]-benzoyl-L-glutamate (A) The compound (381 mg) as obtained in Example 5 was dissolved in trifluoroacetic acid (3 ml), and the solution was stirred at room temperature for 3 hours. The trifluoroacetic acid was distilled off under reduced pressure, followed by drying at 70° C. under reduced pressure, and the resulting residue, together with diethyl L-glutamate hydrochloride (748 mg) was suspended in dimethylformamide (4 ml). A dimethylformamide solution (4 ml) of diphenylphosphoryl azide (858 mg) was added to the suspension at 0° C., followed by stirring, and a dimethylformamide solution (4 ml) of triethylamine (631 mg) was added dropwise to the solution mixture at the same temperature, followed by stirring at 0° C. for 30 minutes and then at room temperature for 63 hours. The solvent was distilled off under reduced pressure, and the resulting residue was purified by column chromatography (15 g of silica gel; dichloromethane separated from conc. ammonia→dichloromethane separated from conc. ammonia-ethanol=40:1→30:1) to give the subject compound (374 mg) in the form of colorless crystals.

(B) By following the same procedure as described in Example 2, the subject compound can be produced from the compound as obtained in Example 4.

IR (KBr): 3330, 3160, 1735, 1632, 1575, 1540, 1500, 1200 cm$^{-1}$.

$^1$H-NMR (Me$_2$SO-d$_6$): 1.17(3H,t,J=7 Hz), 1.20(3H,t,J=7 Hz), 1.80–2.20(4H,m), 2.44(2H,t,J=7 Hz), 2.68(2H,t,J=7 Hz), 2.72(2H,t,J=7Hz), 4.05(2H,q,J=7Hz), 4.11(2H,q,J=7Hz), 4.35–4.50(1H,m), 5.34(2H,s), 5.91(2H,s), 6.42(1H,s), 7.31(2H,d,J=8 Hz), 7.80(2H,d,J=8 Hz), 8.66(1H,d,J=8 Hz), 10.51(1H,s).

EXAMPLE 7

Production of N-[4-[3-(2,4-diamino-7H-pyrrolo[2,3d]pyrimidin-5-yl)propyl]benzoyl]-L-glutamic acid By following the same procedure as described in Example 3, the compound as obtained in Example 6 was subjected to a hydrolysis reaction to give the subject compound (201 mg) in the form of white crystals. m.p. 220°–221° C.

IR (KBr): 3340, 3200, 2940, 1660–1630, 1540, 1500, 1397 cm$^{-1}$.

$^1$H-NMR (Me$_2$SO-d$_6$): 1.75–2.20(4H,m), 2.35(2H,t,J=7 Hz), 2.68(2H,t,J=7 Hz), 2.71(2H,t,J=7 Hz), 4.30–4.47(1H, m), 5.53(2H,brs), 6.15(2H,s), 6.46(1H,s), 7.31(2H,d,J=8 Hz), 7.81(2H,d,J=8 Hz), 8.48(1H,d,J=8 Hz), 10.51(1H,s).

EXAMPLE 8

Production of tert-butyl 4-[5-(2,4,6-triaminopyrimidin-5-yl)-6,6-dimethoxyhexyl]benzoate By following the same procedure as described in Example 1, the compound (378 mg) as obtained in Reference Example 6 was reacted with guanidine hydrochloride to give the subject compound (433 mg) in the form of white crystals.

IR (KBr): 3475, 3360, 3220, 2975, 2930, 1715, 1640, 1607, 1563, 1435, 843, 800 cm$^{-1}$.

$^1$H-NMR (CDCl$_3$): 1.14–1.32(2H,m), 1.45–1.72(3H,m), 1.58(9H,s), 1.86–2.04(1H,m), 2.56–2.68(2H,m), 2.72–2.83 (1H,m), 3.47(3H,s), 3.52(3H,s), 4.39(1H,d,J=3 Hz), 4.36(2H,brs), 4.48(2H ,brs), 5.21(2H,brs), 7.18(2H,d,J=8 Hz), 7.88(2H,d,J=8 Hz).

EXAMPLE 9

Production of diethyl N-[4-[4-(2,4-diamino-7H-pyrrolo[2,3-d]pyrimidin-5-yl)butyl]benzoyl]-L-glutamate By following the same procedure as described in Example 2, the compound (230 mg) as obtained in Example 8 yielded the subejct compound (228 mg) in the form of white powder.

IR (KBr): 3380, 3200, 2980, 2930, 1735, 1640, 1605, 1572 cm$^{-1}$.

1H-NMR (CDCl$_3$/CD$_3$OD): 1.22(3H,t,J=7 Hz), 1.31(3H, t,J=7 Hz), 1.60–1.83(4H,m), 2.43–2.51(2H,m), 2.63–2.76(4H,m), 4.11(2H,q,J=7 Hz), 4.24(2H,q,J=7 Hz), 4.74–4.86(1H,m), 6.45(1H,s), 7.24(2H,d,J=8 Hz), 7.74(2H, d,J=8 Hz).

EXAMPLE 10

Production of
N-[4-[4-(2,4-diamino-7H-pyrrolo[2,3-d]
pyrimidin-5-yl)butyl]benzoyl]-L-glutamic acid By following the same procedure as described in Example 3, the compound (103 mg) as obtained in Example 9 was subjected to a hydrolysis reaction to give the subject compound (72 mg) in the form of white crystals.

IR (KBr): 3340, 3200, 2930, 165 0, 1635, 1540 cm$^{-1}$.

$^1$H-NMR (Me$_2$SO-d$_6$): 1.45–1.76(4H,m), 1.88–2.19(2H, m), 2.29–2.43(2H,m), 2.58–2.76(4H,m), 4.32–4.46(1H,m), 5.54(2H,brs), 6.16(2H,brs), 6.42(1H,s), 7.29(2H,d,J=8 Hz), 7.79(2H,d,J=8 Hz), 8.52(1H,d,J=7 Hz), 10.48(1H,brs).

EXAMPLE 11

Production of diethyl
N-[4-[3-(2,4-diamino-6,7-dihydro-5H-pyrrolo[
2,3-d]pyrimidin-5-yl)propyl]benzoyl]-L-glutamate The compound (20 mg) as obtained Example 9 was dissolved in 2% hydrochloric-acid ethanol solution (20 ml), and after addition of platinum oxide (3 mg), catalytic reduction was carried out under hydrogen atmosphere for 12 hours. The catalyst was removed by filtration, and the filtrate was concentrated to dryness. The resulting residue was purified by column chromatography (2.0 g of silica gel; dichloromethane separated from conc. ammonia dichloromethane separated from conc. ammonia-ethanol=40:1→ 30:1) to give the subject compound (4.8 mg).

IR (KBr): 3350, 2990, 2945, 1740, 1610, 1540, 1508, 1438 cm$^{-1}$.

$^1$H-NMR (CDCl$_3$) 1.23(6H,t×2,J=7 Hz), 1.43–1.80(3H, m), 1.85–2.77(7H,m), 2.95–3.30(2H,m), 3.58(1H,t,J=11 Hz), 4.07 (2H,q,J=7 Hz), 4.20(2H,q,J=7 Hz), 4.25(1H,brs), 4.63–4.83 (1H,m), 4.68(1H,brs), 7.00–7.23(1H,m), 7.13(2H,d,J=8 Hz), 7.67 (2H,d,J=8 Hz).

EXAMPLE 12

Production of
N-[4-[3-(2,4-diamino-6,7-dihydro-5H-pyrrolo[ 2,3-d
]pyrimidin-5-yl)propyl]benzoyl]-L-glutamic acid By following the same procedure as described in Example 3, the compound (4.4 mg) as obtained in Example 11 was subjected to a hydrolysis reaction to give the subject compound (3.2 mg).

IR (KBr): 3700–2350, 3215, 1690–1620, 1540 cm$^{-1}$.

$^1$H-NMR (Me$_2$SO-d$_6$): 1.02–1.85(4H,m), 1.85–2.83(6H, m), 2.90–3.30(2H,m), 3.55(1H,t,J=11 Hz), 4.15–4.45(1H, m), 6.38 (2H,brs), 6.77(2H,brs), 6.90(1H,brs), 7.22(2H,d, J=8 Hz), 7.74(2H,d,J=8 Hz), 8.22 (1H,d,J=7 Hz) .

EXAMPLE 13

Production of ethyl
4-[4-(2,4,6-triaminopyrimidin-5-yl)-
5,5-dimethoxypentyl]benzoate Under argon atmosphere, a solution (0.612 ml) of 1.0 mole of sodium ethoxide in ethyl alcohol was added to a suspension (1.0 ml) of guanidine hydrochloride (58.5 mg) in ethyl alcohol. To this solution, a solution (3.0 ml) of ethyl 4-[5,5-dicyano-4-(dimethoxymethyl)pentyl]benzoate* (190 mg) in ethyl alcohol was added and the mixture was refluxed under heating for 2 hours.

*Obtained from ethyl 4-(4-oxobutyl)benzoate according to Reference Examples 3 and 2.

The reaction mixture was poured into water (10 ml), extracted with dichloromethane, and the organic layer was dried with anhydrous sodium sulfate. Solvent was removed from the extract by distillation under reduced pressure and the residue was purified by flash column chromatography (15 g of silica gel; dichloromethane-methanol=30:1→15:1) to give the subject compound (214 mg).

IR(KBr): 3460, 3340, 3180, 2940, 1710, 1610, 1565, 1435, 1275, 1110, 1060, 805 cm$^{-1}$.

$^1$H-NMR(CDCl$_3$): 1.38(3H,t,J=7.2 Hz), 1.43–1.70(3H, m), 1.83–2.05(1H,m), 2.63(2H,t,J=7 Hz), 2.77–2.87(1H,m), 3.46(3H,s), 3.50(3H,s), 4.36(2H,q,J=7.2 Hz), 4.37(1H,d,J= 3.6 Hz), 4.45(4H,brs), 5.10(2H,brs), 7.20(2H,d,J=8 Hz), 7.94(2H,d,J=8 Hz)

EXAMPLE 14

Production of ethyl 4-[3-(2,4-diamino-7H-pyrrolo[2, 3-d]pyrimidin-5-yl)propyl]benzoate To the suspension (2.0 ml) of the product in Example 13 (404 mg) in ethyl alcohol, ethyl alcohol containing 20% (w/w) of hydrogen chloride (2.0 ml) and water (0.02 ml) were added, and the mixture was stirred at room temperature for 2 hours. The reaction mixture was diluted with water (10 ml) and made alkaline by adding aqueous ammonia thereto, followed by removing most part of ethyl alcohol therefrom by distillation under reduced pressure. Resulting precipitates were collected by filtration, washed with water, alcohol and ether, successively, and dried to give the subject compound (300 mg).

IR(KBr): 3330, 3225, 2930, 1705, 1610, 1575, 1490, 1450, 1410, 1280, 1180, 1105, 1020, 830 cm$^{-1}$.

$^1$H-NMR(CDCl$_3$/CD$_3$OD): 1.39(3H,t,J=7.2 Hz), 2.05(2H,m), 2.67(2H,t,J=7.2 Hz ), 2.78(2H,t,J=7.2 Hz), 4.37(2H, q,J=7.2 Hz), 6.50(1H,s), 7.27(2H,d,J=8 Hz), 7.98(2H,d,J=8 Hz)

EXAMPLE 15

Production of 4-[3-(2,4-diamino-7H-pyrrolo[2,3d] pyrimidin-5-yl)propyl]benzoic acid The product of Example 14 (340 mg) was suspended in a mixed solution of tetrahydrofuran-water (5:1, 6.0 ml), 1N aqueous solution of sodium hydroxide (4.0 ml) was added thereto, and the mixture was stirred at 50° C. for 18 hours. Most part of tetrahydrofuran was removed from the mixture by distillation under reduced pressure and the residue was neutralized by adding 1N hydrochloric acid thereto. Resulting precipitates were collected by filtration, washed with water, methanol and ether, successively, and dried under reduced pressure to give the subject compound (305 mg).

IR(KBr): 3480, 3390, 3130, 2940, 1650, 1605, 1550, 1460, 1390, 1255, 1180, 1095, 980, 780 cm$^{-1}$.

$^1$H-NMR(Me$_2$SO-d$_6$): 1.73–1.95(2H,m), 2.67(2H,t,J=7 Hz), 2.71(2H,t,J=7 Hz), 5.37(2H,s), 5.95(2H,s), 6.43(1H,s), 7.33(2H,d,J=8 Hz), 7.86(2H,d,J=8 Hz), 10.40(1H,s)

EXAMPLE 16

Production of diethyl
N-[4-[3-(2,4-diamino-7H-pyrrolo[
2,3-d]pyrimidin-5-yl)propyl]benzoyl]-L-glutamate The product of Example 15 (339 mg) and diethyl L-glutamate hydrochloride (748 mg) were suspended in dimethylformamide (4.0 ml), a solution (4.0 ml) of diphenylphosphoryl azide (858 mg) in dimethylformamide was added thereto at 0° C. and stirred. Subsequently, a solution (4.0 ml) of triethylamine (631 mg) in dimethylformamide was added dropwise thereto at the same temperature, and the mixture was stirred at 0° C. for 30 minutes and then at room temperature for 63 hours, followed by removing solvent by distillation under reduced pressure. Resulting residue was purified by column chromatography (15 g of silica gel; dichloromethane separated from conc. ammonia dichloromethane separated from conc. ammonia-ethanol=40:1 30:1) to give the Subject compound (386 mg) as colorless crystals.

IR(KBr) and $^1$H-NMR(Me$_2$SO-d$_6$) of the compound were completely identical with those of the product in Example 6.

EXAMPLE 17

Production of diethyl N-[4-[4-(2,4,6-triaminopyrimidin-5-yl)-5,5-dimethoxypentyl]benzoyl]-L-glutamate The product of Example 13 (403 mg) was suspended in a mixed solution of tetrahydrofuran-water (5:1, 8.0 ml), 1N aqueous solution of sodium hydroxide (2.0 ml) was added thereto and the mixture was stirred at 40° C. overnight. After neutralizing the mixture by adding 1N hydrochloric acid (2.0 ml), solvent was removed by distillation under reduced pressure and the residue was dried to give crude 4-[4-(2,4,6-triaminopyrimidin-5-yl)-5,5-dimethoxypentyl]benzoic acid. The total amount of the crude product and diethyl glutamate hydrochloride (360 mg) were suspended in dimethylformamide (4.0 ml), a solution (4.0 ml) of diethyl phosphorocyanidate (171 mg) in dimethylformamide was added thereto at 0° C. and the mixture was stirred. Subsequently, a solution (4.0 ml) of triethylamine (303 mg) in dimethylformamide was added dropwise thereto at the same temperature and the mixture was stirred at 0° C. for 30 minutes and then at room temperature for 3 hours, followed by removing solvent by distillation under reduced pressure. The resulting residue was purified by flash column chromatography (15 g of silica gel; dichloromethane-methano 30:1→75:1) to give the subject compound (417 mg).

$^1$H-NMR (CDCl$_3$/CD$_3$OD): 1.22(3H,t,J=7 Hz), 1.32(3H, t,J=7 Hz), 1.52–1.74(2H,m), 1.93–2.38(4H,m), 2.45–2.56(2H,m), 2.63(2H,t,J=7.4 Hz), 2.77–2.87(1H,m), 3.48(3H,s), 3.51(3H,s), 4.12(2H,q,J=7 Hz), 4.25(2H,q,J=7 Hz), 4.35(1H,d,J=3.2 Hz), 4.77–4.85(1H,m), 7.21(1H,d,J=8.4 Hz), 7.94(2H,d,J=8.4 Hz)

EXAMPLE 18

Production of diethyl N-[4-[3-(2,4-diamino-7H-pyrrolo[2,3-d]pyrimidin-5-yl)propyl]benzoyl]-L-glutamate To a suspension of the product of Example 17 (100 mg) in ethyl alcohol (2.0 ml), ethyl alcohol containing 20% (w/w) of hydrogen chloride (2.0 ml) and water (0.02 ml) were added and the mixture was heated at room temperature for 2 hours. The reaction mixture was diluted with water (10 ml), and neutralized by adding aqueous ammonia thereto, followed by removing solvent therefrom by distillation under reduced pressure. The resulting residue was purified by column chromatography (15 g of silica gel; dichloromethane separated from conc. ammonia→dichloromethane separated from conc. ammonia-ethanol=40:1→ 30:1) to give the subject compound (68 mg).

IR(KBr) and $^1$H-NMR(Me$_2$SO-d$_6$) of the compound were identical with those of the product in Example 6.

Production of 4-[3-(2,4-diamino-7H-pyrrolo[2,3-d]pyrimidin-5-yl)propyl]benzoic acid Methyl 4-[4-(2,4,6-triaminopyrimidin-5-yl)-5,5-dimethoxypentyl] bezoate (2.15 g), obtained from methyl 4-4-(4-oxobutyl)benzoate employing procedures of Reference Example 3, Reference Example 2 and Example 13 in this order, was dissolved in a mixed solution of tetrahydrofuran (15.5 ml) and 1N hydrochloric acid (7.1 ml), and the mixture was stirred at 68° C. for 1 hour. Methyl 4-[3-(2,4-diamino-7H-pyrrolo[3,2-d]pyrimidin-5-yl)propyl]benzoate produced in the reaction mixture was not isolated in this stage. To the reaction mixture, methanol (5.7 ml) and an aqueous solution (2.85 ml) of sodium hydroxide (0.684 g) were directly added and hydrolysis was carried out at 67° C. for 1 hour. Organic solvent in the reaction mixture was removed by distillation under reduced pressure to remain aqueous solution which was adjusted to pH 3 with 6N hydrochloric acid. Resulting precipitates were collected by filtration, washed with a small amount of water and dried under reduced pressure to give the subject compound (1.72 g). IR(KBr) and H-NMR(Me$_2$SO-d$_6$) of the compound were completely identical with the product of Example 15.

In the same manner as in Examples 1 to 19, the following compounds can be synthesized.

(1) Dibenzyl N-[4-[3-(2-amino-4-hydroxy-7H-pyrrolo[2,3-d] pyrimidin-5-yl)propyl]benzoyl]-L-glutamate,
(2) N-[4-[3-(2-amino-4-hydroxy-7H-pyrrolo[2,3-d]pyrimidin- 5-yl)propyl]benzoyl]-L-glutamic acid,
(3) N-[4-[3-(2-amino-4-hydroxy-6,7-dihydro-5H-pyrrolo[2, 3-d] pyrimidin-5-yl)propyl]benzoyl]-L-glutamic acid,
(4) Di(p-methoxybenzyl) N-[4-[3-(2-amino-4-mercapto-7H-pyrrolo( 2,3-d]pyrimidin-5-yl)propyl]benzoyl]-L-glutamate,
(5) N-[4-[3-(2-amino-4-mercapto-7H-pyrrolo[2,3-d]pyrimidin-5-yl)propyl]benzoyl]-L-glutamic acid,
(6) N-[4-[3-(2-amino-4-mercapto-6,7-dihydro-5H-pyrrolo [2,3
(7) N-[4-[3-(2,4-diamino-6-methyl-7H-pyrrolo[2,3-d]pyrimidin- 5-yl)propyl]benzoyl]-L-glutamic acid,
(8) N-[4-[3-(2,4-diamino-6-methyl-6,7-dihydro-5H-pyrrolo [2,3-d] pyrimidin-6-yl)propyl]benzoyl]-L-glutamic acid,
(9) N-[4-[3-(2,4-diamino-6-ethyl-7H-pyrrolo[2,3-d]pyrimidin- 5-yl)propyl]benzoyl]-L-glutamic acid,
(10) N-[4-[3-(2,4-diamino-6-ethyl-6,7-dihydro-5H-pyrrolo [2,3-d] pyrimidin-5-yl)propyl]benzoyl]-L-glutamic acid,
(11) N-[4-[3-(2,4-diamino-6-vinyl-7H-pyrrolo[2,3-d] pyrimidin-5-yl)propyl]benzoyl]-L-glutamic acid,
(12) N-[4-[3-(2,4-diamino-6-ethynyl-7H-pyrrolo[2,3-d] pyrimidin-5-yl)propyl]benzoyl]-L-glutamic acid,
(13) N-[4-[3-2,4-diamino-6-hydroxymethyl-7H-pyrrolo[2, 3-d] pyrimidin-5-yl)propyl]benzoyl]-L-glutamic acid,
(14) N-[4-[3-(2,4-diamino-7H-pyrrolo[2,3-d]pyrimidin-5-yl)-1-methylpropyl] benzoyl]-L-glutamic acid,
(15) N-[4-[3-(2,4-diamino-6,7-dihydro-5H-pyrrolo[2,3-d] pyrimidin-5-yl)-1-methylpropyl]benzoyl]-L-glutamic acid,
(16) N-[4-[3-(2,4-diamino-7H-pyrrolo[2,3-d]pyrimidin-5-yl)- 1-hydroxymethylpropyl]benzoyl]-L-glutamic acid,
(17) N-[4-[3-(2,4-diamino-7H-pyrrolo[2,3-d]pyrimidin-5-yl)-1-(formylmethyl)propyl]benzoyl]-L-glutamic acid,
(18) N-[4-[3-(2,4-diamino-7H-pyrrolo[2,3-d]pyrimidin-5-yl)-1-chloromethylpropyl] benzoyl]-L-glutamic acid,

(19) N-[4-[3-(2,4-diamino-7H-pyrrolo[2,3-d]pyrimidin-5-yl)-1-dichloromethylpropyl]benzoyl]-L-glutamic acid,
(20) N-[4-[3-(2,4-diamino-7H-pyrrolo[2,3-d]pyrimidin-5-yl)-1-trifluoromethylpropyl]benzoyl]-L-glutamic acid,
(21) N-[4-[3-(2,4-diamino-7H-pyrrolo[2,3-d]pyrimidin-5-yl)-1-methoxymethylpropyl]benzoyl]-L-glutamic acid,
(22) N-[4-[3-(2,4-diamino-7H-pyrrolo[2,3-d]pyrimidin-5-yl)-1-ethoxymethylpropyl]benzoyl]-glutamic acid,
(23) N-[4-[3-(2,4-diamino-7H-pyrrolo[2,3-d]pyrimidin-5-yl)-1-cyanomethylpropyl]benzoyl]-L-glutamic acid,
(24) N-[4-[3-(2,4-diamino-7H-pyrrolo[2,3-d]pyrimidin-5-yl)-1-(methylthiomethyl)propyl]benzoyl]-L-glutamic acid,
(25) N-[4-[3-(2,4-diamino-7H-pyrrolo[2,3-d]pyrimidin-5-yl)-2-methylpropyl]benzoyl]-L-glutamic acid,
(26) N-[4-[3-(2,4-diamino-7H-pyrrolo[2,3-d]pyrimidin-5-yl)-3-methylpropyl] benzoyl]-L-glutamic acid,
(27) N-[4-[3-(2,4-diamino-7H-pyrrolo[2,3-d]pyrimidin-5-yl)-1,1-dimethylpropyl]benzoyl]-L-glutamic acid,
(28) N-[4-[3-(2,4-diamino-6,7-dihydro-5H-pyrrolo[2,3-d]-pyrimidin-5-yl)-1,1-dimethylpropyl]benzoyl]-L-glutamic acid,
(29) N-[4-[3-(2,4-diamino-7H-pyrrolo[2,3-d]pyrimidin-5-yl)-2,2-dimethylpropyl]benzoyl]-L-glutamic acid,
(30) N-[4-[3-(2,4-diamino-7H-pyrrolo[2,3-d]pyrimidin-5-yl)-1-ethylpropyl] benzoyl]-L-glutamic acid,
(31) N-[4-[3-(2,4-diamino-6,7-dihydro-5H-pyrrolo[2,3-d]pyrimidin-5-yl)-1-ethylpropyl]benzoyl]-L-glutamic acid,
(32) N-[4-[3-(2,4-diamino-7H-pyrrolo[2,3-d]pyrimidin-5-yl)-1-(2-hydroxyethyl)propyl]benzoyl]-L-glutamic acid,
(33) N-[4-[3-(2,4-diamino-7H-pyrrolo[2,3-d]pyrimidin-5-yl)-1-( 2-formylethyl)propyl]benzoyl]-L-glutamic acid,
(34) N-[4-[3-(2,4-diamino-7H-pyrrolo[2,3-d]pyrimidin-5-yl)-1-(2-methoxyethyl)propyl]benzoyl]-L-glutamic acid,
(35) N-[4-[3-(2,4-diamino-7H-pyrrolo[2,3-d]pyrimidin-5-yl)-1-(2-ethoxyethyl)propyl]benzoyl]-L-glutamic acid,
(36) N-[4-[3-(2,4-diamino-7H-pyrrolo[2,3-d]pyrimidin-5-yl)-2-ethylpropyl] benzoyl]-L-glutamic acid,
(37) N-[4-[3-(2,4-diamino-7H-pyrrolo[2,3-d]pyrimidin-5-yl)-1-vinylpropyl] benzoyl]-L-glutamic acid,
(38) N-[4-[3-(2,4-diamino-7H-pyrrolo[2,3-d]pyrimidin-5-yl)-2-vinylpropyl] benzoyl]-L-glutamic acid,
(39) N-[4-[3-(2,4-diamino-7H-pyrrolo[2,3-d]pyrimidin-5-yl)-1-allylpropyl] benzoyl]-L-glutamic acid,
(40) N-[4-[3-(2,4-diamino-7H-pyrrolo[2,3-d]pyrimidin-5-yl)-1-ethynylpropyl] benzoyl]-L- glutamic acid,
(41) N-[4-[3-(2,4-diamino-7H-pyrrolo[2,3-d]pyrimidin-5-yl)-1-(iso-propyl)Propyl] benzoyl]-L-glutamic acid,
(42) N-[4-[3-(2,4-diamino-7H-pyrrolo[2,3-d]pyrimidin-5-yl)-1-(2-propenyl)propyl]benzoyl]-L-glutamic acid,
(43) N-[4-[3-(2,4-diamino-7H-pyrrolo[2,3-d]pyrimidin-5-yl)-1-propargylpropyl] benzoyl]-L-glutamic acid,
(44) N-[4-[3-(2,4-diamino-7H-pyrrolo[2,3-d]pyrimidin-5-yl)-1-( 2-propynyl)propyl]benzoyl]-L-glutamic acid,
(45) Methyl 4-[4-(2,4,6-triaminopyrimidin-5-yl)-5,5-dimethoxypentyl]benzoate,
(46) Benzyl 4-[4-(2,4,6-triaminopyrimidin-5-yl)-5,5-dimethoxypentyl]benzoate,
(47) p-Methoxybenzyl 4-[4-(2,4,6-triaminopyrimidin-5-yl)-5,5-di(methylthio)pentyl]benzoate,
(48) Dibenzyl N-[4-[4-(2,4,6-triaminopyrimidin-5-yl)- 5,5-dimethoxypentyl]benzoyl]-L-glutamate.
(49) Methyl 4-[3-(2,4-diamino-7H-pyrrolo[2,3-d]pyrimidin-5-yl)propyl]benzoate,
(50) Benzyl 4-[3-(2,4-diamino-7H-pyrrolo[2,3-d]pyrimidin-5-yl))propyl]benzoate.

What is claimed is:

1. A compound represented by the formula:

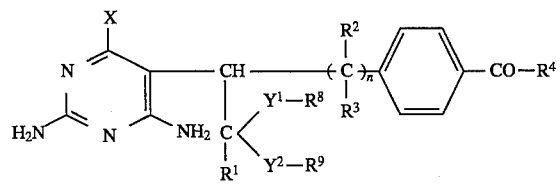

wherein

X represents an amino, hydroxyl, or mercapto group;

$R^1$ represents hydrogen or a $C_{1-6}$ alkyl group which may be substituted;

$R^2$ and $R^3$ each, being the same or different from each other, and which may be different individually in the n repeating units, represents hydrogen or a $C_{1-6}$ alkyl, $C_{2-6}$ alkenyl, or $C_{2-6}$ alkynyl group, any of which may be substituted;

$R^4$ represents $OR^5$ wherein $R^5$ represents hydrogen or a hydrocarbon group selected from the group consisting of $C_{1-5}$ alkyl, benzyl, and phenyl any which may be substituted or $NHCH(COOR^6)CH_2CH_2COOR^7$ wherein $R^6$ and $R^7$ each represents hydrogen or a hydrocarbon group selected from the group consisting of $C_{1-5}$ alkyl, benzyl, and phenyl which may be substituted;

n represents an integer from 1 to 4;

$Y^1$ and $Y^2$ are independently oxygen or sulfur;

$R^8$ and $R^9$ independently represents hydrogen or a hydrocarbon group selected from the group consisting of $C_{1-5}$ alkyl, benzyl, and phenyl any which may be substituted;

or a salt thereof;

wherein in the above formulae, the substituted alkyl, substituted alkenyl and substituted alkynyl groups of $R^1$, $R^2$, $R^3$, $R^5$, $R^6$, $R^7$, $R^8$ and $R^9$ are substituted with one to three substituents selected from the group consisting of halogen, nitro, cyano, alkoxy of 1 to 4 carbon atoms, alkanoyl of 1 to 4 carbon atoms, and alkanoyloxy of 1 to 4 carbon atoms, alkoxycarbonyl of 2 to 4 carbon atoms, trifluoromethyl, alkylthio of 1 to 4 carbon atoms, alkylsulfinyl of 1 to 4 carbon atoms and alkylsulfonyl of 1 to 4 carbon atoms; and wherein the substituted phenyl and substituted benzyl groups of $R^5$, $R^6$, $R^7$, $R^8$ and $R^9$ are substituted with one to three substituents selected from the group consisting of halogen, nitro, cyano, alkoxy of 1 to 4 carbon atoms, alkanoyl of 1 to 4 carbon atoms, alkanoyloxy of 1 to 4 carbon atoms, alkoxycarbonyl of 2 to 4 carbon atoms, trifluoromethyl, alkylthio of 1 to 4 carbon atoms, alkylsulfinyl of 1 to 4 carbon atoms, alkylsulfonyl of 1 to 4 carbon atoms alkyl of 1 to 4 carbon atoms, alkenyl of 2 to 3 carbon atoms, and alkynyl of 2 to 3 carbon atoms.

2. A compound as claimed in claim 1, wherein $R^1$, $R^2$, and $R^3$ are each hydrogen.

3. A compound as claimed in claim 1, wherein $Y^1$ and $Y^2$ are both oxygen atoms.

4. A compound as claimed in claim 1, wherein $R^8$ and $R^9$ are each independently a $C_{1-3}$ alkyl group.

5. A compound as claimed in claim 1, wherein $R^5$, $R^6$, and $R^7$ are each independently a $C_{1-5}$ alkyl group or benzyl group.

6. A compound as claimed in claim 1, wherein X is an amino group.

7. A compound as claimed in claim 1, wherein X is a hydroxyl group.

8. A compound as claimed in claim 1, wherein X is a mercapto group.

9. A compound as claimed in claim 1, wherein n is 2 or 3.

10. A compound as claimed in claim 1, wherein $R^5$, $R^6$, and $R^7$ each are independently a $C_{1-3}$ alkyl group.

11. A compound as claimed in claim 1, wherein one or both of $Y^1$ and $Y^2$ are oxygen.

12. A compound as claimed in claim 1, wherein one or both $Y^1$ and $Y^2$ are sulfur.

13. A compound as claimed in claim 1, wherein $R^8$ and $R^9$ are each independently a $C_{1-5}$ alkyl group.

* * * * *